United States Patent
Yamamoto

(10) Patent No.: US 6,312,410 B1
(45) Date of Patent: *Nov. 6, 2001

(54) AUXILIARY APPLIANCE FOR SYRINGE FIXATION

(75) Inventor: Tetsuya Yamamoto, Osaka (JP)

(73) Assignee: Sugan Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/606,249

(22) Filed: Feb. 23, 1996

(30) Foreign Application Priority Data

Oct. 30, 1995 (JP) .................................................. 7-282129

(51) Int. Cl.⁷ ..................................................... A61M 1/00
(52) U.S. Cl. ........................................... 604/152; 604/131
(58) Field of Search .................................. 604/131, 134, 604/140, 143, 151, 152, 218, 227, 228, 181, 187, 154, 232, 155, 905, 283; 128/DIG. 1, 655, 654; 600/432, 433

(56) References Cited

U.S. PATENT DOCUMENTS

| | | | |
|---|---|---|---|
| 4,562,844 | * | 1/1986 | Carpenter et al. .................... 604/220 |
| 4,592,746 | * | 6/1986 | Burkholder et al. .................. 604/187 |
| 5,300,031 | * | 4/1994 | Neer et al. ............................ 604/218 |
| 5,322,511 | * | 6/1994 | Armbruster et al. ................. 604/155 |
| 5,383,858 | * | 1/1995 | Reilly et al. .......................... 604/187 |
| 5,520,653 | * | 5/1996 | Reilly et al. .......................... 604/152 |
| 5,535,746 | * | 7/1996 | Hoover et al. ....................... 604/187 |
| 5,779,675 | * | 7/1998 | Reilly et al. .......................... 604/131 |

FOREIGN PATENT DOCUMENTS

| | | |
|---|---|---|
| 57-179461 | 11/1982 | (JP) . |
| 6-7440 | 1/1994 | (JP) . |
| 6-7444 | 1/1994 | (JP) . |
| 6-154322 | 6/1994 | (JP) . |
| 6-507324 | 8/1994 | (JP) . |
| 6-339528 | 12/1994 | (JP) . |

OTHER PUBLICATIONS

Brochure "Angiomat CT", Digital Injection System For Enhanced CT Scan, 6 Pages, 1988.

* cited by examiner

Primary Examiner—Angela D. Sykes
(74) Attorney, Agent, or Firm—McDermott, Will & Emery

(57) ABSTRACT

An auxiliary appliance for syringe fixation according to the present invention comprises a syringe adaptor for fixing a flange part of a syringe to an injection head, and a piston adaptor for connecting a piston to a plunger. Thus, it is possible to attach a syringe, having a different shape from a syringe which can be directly mounted on the injection head, to the injection head.

5 Claims, 11 Drawing Sheets

AUXILIARY APPLIANCE FOR SYRINGE FIXATION

BACKGROUND OF THE INVENTION

1. Field of the Invention

The present invention relates to an auxiliary appliance for syringe fixation, and more specifically, it relates to the structure of an auxiliary appliance for syringe fixation for attaching a syringe which is filled up with a contrast medium to an injection head in a medical field.

2. Description of the Background Art

In recent years, various means for testing functions of human bodies have been developed. One of such means is angiography employing a high-speed scan CT for diagnosing the functions of circulatory organs of a human body. The angiography employing a CT is adapted to inject a contrast medium into a patient's body for diagnosing the functions of the circulatory organs through the contrast medium which is injected into the patient's body with the CT.

FIG. 11 shows an injection head 10, which is generally employed for injecting a contrast medium into a human body. A syringe 300 which is previously filled up with a contrast medium is attached to the injection head 10, and a piston 300d provided in the syringe 300 is gradually moved toward the forward end of the syringe 300 with a plunger 11 which is provided in the injection head 10, as shown in FIG. 12. Thus, the contrast medium is injected into the human body through a tube 301 which is attached to the forward end of the syringe 300 and a catheter or a winged needle (not shown).

The structure of the syringe 300 is now described with reference to FIG. 13.

This syringe 300 has a cylindrical shape, so that an internal space which is defined by the piston 300d is filled up with the contrast medium. An injection port 300a having a tapered front end is provided on the forward end of the syringe 300. The syringe 300 is further provided on its rear end with a flange 300b and a pair of convex parts 300c, to be engaged with the injection head 10, which are provided on opposite positions.

On the rear side of the piston 300d, connection parts 300f to be connected with an oval connection part which is formed on the forward end of a plunger 11 provided on the injection head 10 are provided on positions rotated by 90° with respect to the convex parts 300c to be opposed to each other.

With reference to FIGS. 14 and 15, attachment of the syringe 300 to the injection head 10 is now described.

As shown in FIG. 14, the injection head 10 is provided with an opening 12 having an inner peripheral surface 14. Convex parts 13 to be engaged with the convex parts 300c which are provided on the syringe 300 are provided on opposite positions of the inner peripheral surface 14.

Further, the plunger 11 is arranged in the opening 12, to be connected with the piston 300d of the syringe 300 for moving the piston 300d toward the forward end of the syringe 300.

The plunger 11 is provided on its forward end with a connection part including a neck portion which is smaller than the diameter of the plunger 11 and an oval head portion 11a, which is connected with the neck portion, provided with a curve portion having the same radius of curvature as the body part of the plunger 11.

In the injection head 10 having the aforementioned structure, the syringe 300 is inserted in the opening 12 so that the convex parts 300c provided on the syringe 300 are positioned in concave portions which are defined by the convex parts 13 provided on the opening 12 of the injection head 10, as shown in FIG. 14.

Thereafter the syringe 300 is rotated by about 90° as shown in FIG. 15, whereby the convex parts 300c provided on the syringe 300 are positioned on rear sides of the convex parts 13 provided on the opening 12 so that the convex parts 13 of the opening 12 are engaged with the flange 300b and the convex parts 300c provided on the syringe 300, thereby fixing the syringe 300 to the injection head 10.

At this time, the head portion 11a provided on the plunger 11 is also connected to the connection part 300f which is provided on the piston 300d simultaneously with rotation of the syringe 300.

However, only the syringe 300 having the structure shown in FIG. 13 can be attached to the injection head 10 having the structure shown in FIGS. 14 and 15. On the other hand, a syringe 2 having a structure shown in FIG. 16 is also put on the market, in addition to that shown in FIG. 13.

The syringe 2 shown in FIG. 16 has a cylindrical body part 6, an injection port 7 which is provided on the forward end for injecting a contrast medium, and a flange part 5 which is provided on the rear end for defining an opening. Further, a piston 3 having a female screw 3a on the rear end of the syringe 2 is provided in the body part 6, so that an internal space which is defined by the piston 3 is filled up with a contrast medium 4.

When the syringe 2 shown in FIG. 16 can also be attached to the injection head 10 shown in FIGS. 14 and 15, therefore, it is possible to select two types of syringe shapes in the medical field, thereby improving handiness of persons concerned with medical treatment.

SUMMARY OF THE INVENTION

An object of the present invention is to provide an auxiliary appliance for syringe fixation, which can attach syringes of different shapes to a general injection head.

The present invention is directed to an auxiliary appliance for syringe fixation, for fixing a syringe having a cylindrical body part, comprising an injection port and a flange part defining an opening on front and rear ends thereof respectively, and sealing a liquid in an internal space which is defined by a piston having a connection part on the flange part side in the interior of the body part to an injection head which is provided with an opening having an inner peripheral surface which is provided with an engaging convex part and comprising a plunger having a connection part including a neck portion which is smaller than the diameter of its body part and a substantially oval head portion which is connected to the neck portion with a curve portion having a radius of curvature which is identical to that of the body part on its forward end part for moving the piston in the syringe toward the forward end of the syringe in the opening and injecting the liquid from the syringe through the injection port, and the auxiliary appliance for syringe fixation comprises a flange fixation appliance for fixing the flange part of the syringe to the injection head, and a piston connection appliance for connecting the piston to the plunger.

Thus, it is possible to connect a syringe, having the aforementioned shape which cannot be directly connected to the aforementioned injection head having an opening, to such an injection head through the flange fixation appliance and the piston connection appliance.

Consequently, two types of syringes having different shapes can be attached to a single injection head, whereby it is possible to improve convenience for doctors and nurses in the medical field.

Preferably, the flange fixation appliance comprises a cylindrical body part, a projection which is engaged with the engaging convex part provided on the inner peripheral surface of the opening of the injection head on an end of the body part for fixing the flange fixation appliance itself to the injection head, and a syringe fixation part for fixing the flange part of the syringe on the other end of the body part.

Thus, the projection can be reliably engaged with the engaging convex part which is provided on the inner peripheral surface of the opening of the injection head, whereby the flange fixation appliance itself can be reliably fixed to the injection head. Further, the flange part of the syringe can be reliably fixed to the syringe fixation part.

Further preferably, the syringe fixation part comprises a flange receiving part for supporting the syringe from the rear end and the outer side of the flange part, and a pair of holding members supporting the flange part of the syringe along with the flange receiving part by covering the flange part from the front end of the syringe while holding the body part of the syringe along the outer peripheral surface of the body part.

Thus, the syringe is further reliably fixed to the syringe fixation part, whereby reliability of the auxiliary appliance for syringe fixation can be improved.

Preferably, the piston connection appliance comprises a connected part which is connected to a connection part of the piston on one side thereof, and a connection receiving part for receiving/fixing the connection part which is provided on the forward end of the plunger on another side thereof.

Thus, the piston of the syringe is reliably fixed to the plunger, whereby the movement of the plunger can be reliably transmitted to the piston.

Preferably, the connection receiving part comprises a substantially cylindrical core member having the same radius of curvature as the curve portion of the head portion of the plunger, and a cylindrical rotation member which is rotatable along the outer peripheral surface of the core member, the rotation member has a substantially oval window part of the same shape as the head portion on its one side so that the window part which is capable of receiving the head portion of the connection part of the plunger, and the core member has a groove part which is capable of receiving the head portion on its one side, for fixing the head portion of the plunger to the groove by receiving the head portion after aligning the window part and the groove part with each other and rotating the rotation member by about 90°.

Thus, the plunger and the piston connection appliance are further reliably connected with each other, whereby reliability of the auxiliary appliance for syringe fixation can be improved.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An embodiment of an auxiliary appliance for syringe fixation according to the present invention is now described with reference to the drawings. The shapes of an injection head 10 and a syringe 2 are identical to those of the prior art, and hence redundant description is omitted.

Figure 1:
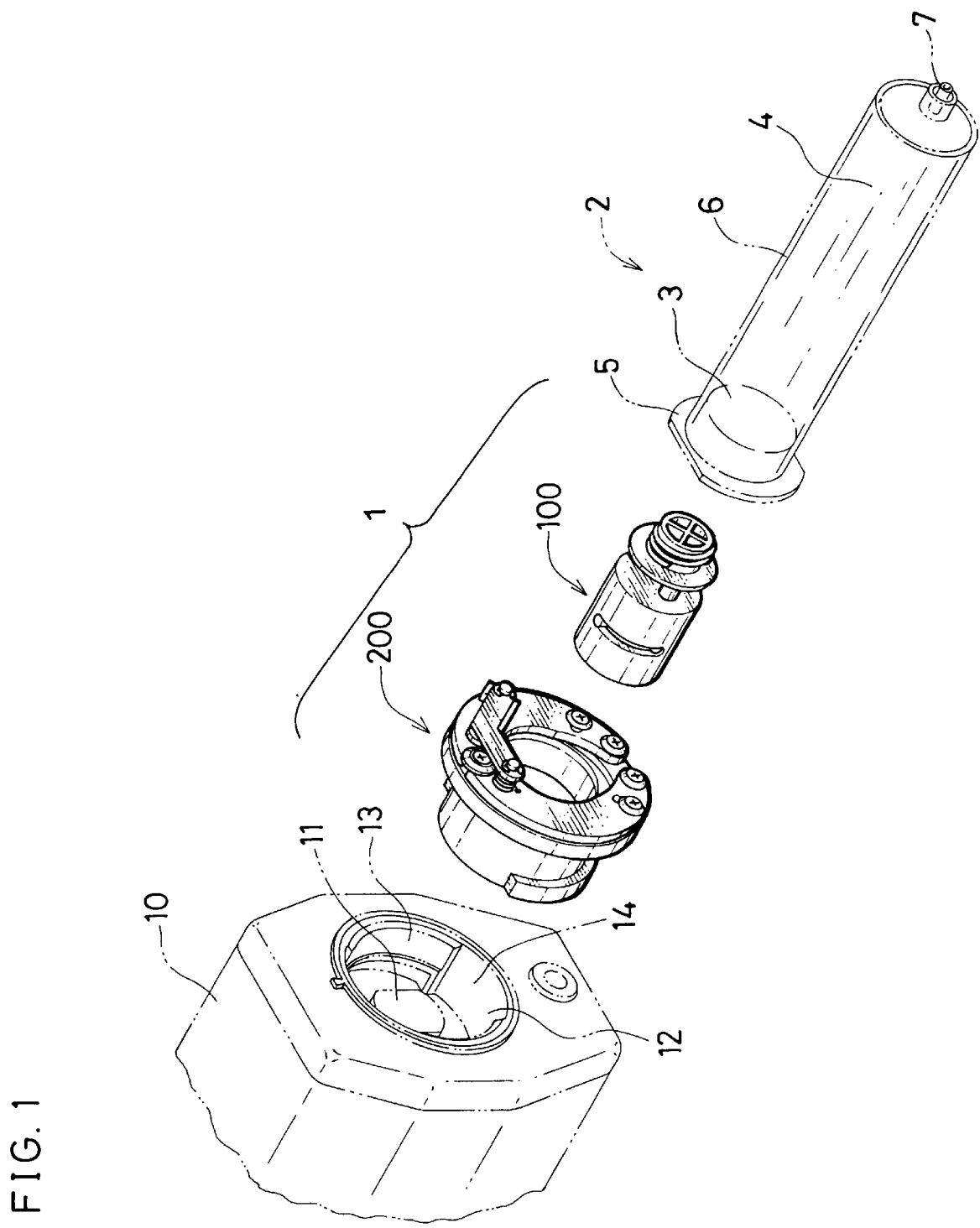
FIG. 1 is a general perspective view showing the structure of an auxiliary appliance for syringe fixation according to the present invention.

Referring to a general perspective view shown in FIG. 1, an auxiliary appliance 1 for syringe fixation according to this embodiment is now schematically described.

The auxiliary appliance 1 for syringe fixation comprises a piston adaptor 100 for connecting a piston 3 of the syringe 2 to a plunger 11 of the injection head 10, and a syringe adaptor 200 for fixing a flange part 5 of the syringe 2 to the injection head 10.

Figure 2:
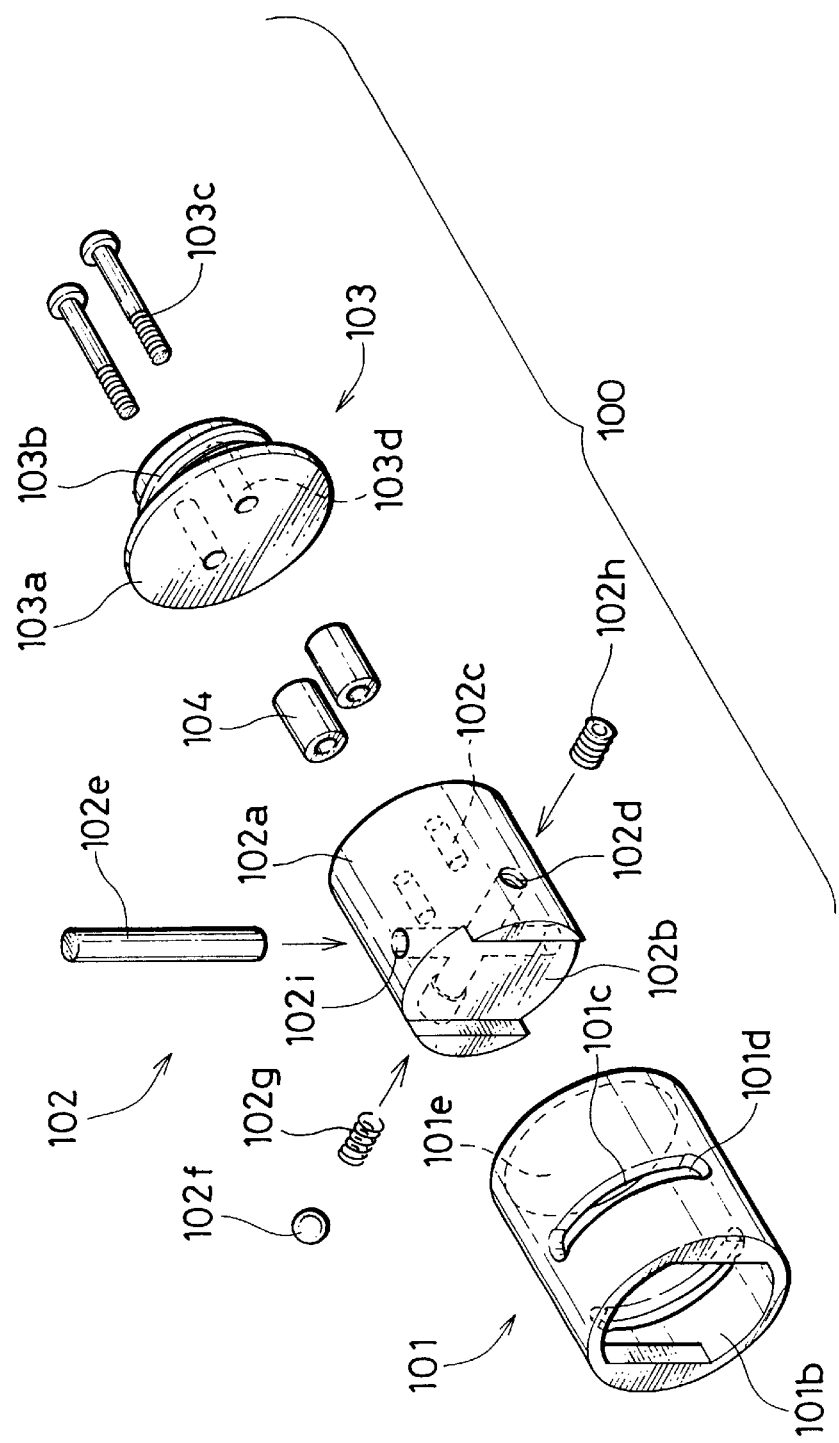
FIG. 2 is a perspective view showing the structure of a piston adaptor according to the present invention.

With reference to FIG. 2, the structure of the piston adaptor 100 is now described. This piston adaptor 100 has a rotation member 101, a core member 102 which is rotatably received in the rotation member 101, and a male screw member 103 which is fixed to the core member 102.

Figure 14:
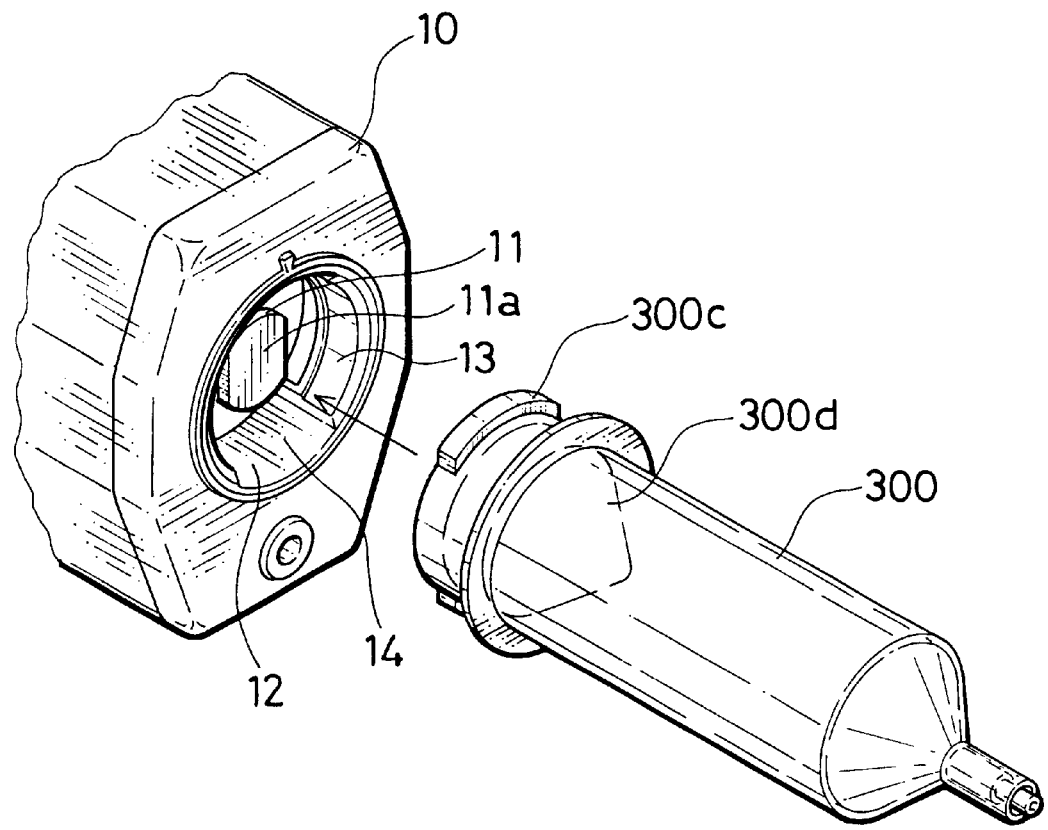
FIGS. 14 and 15 are first and second diagrams showing a state of attaching the syringe to an injection head.
Figure 15:
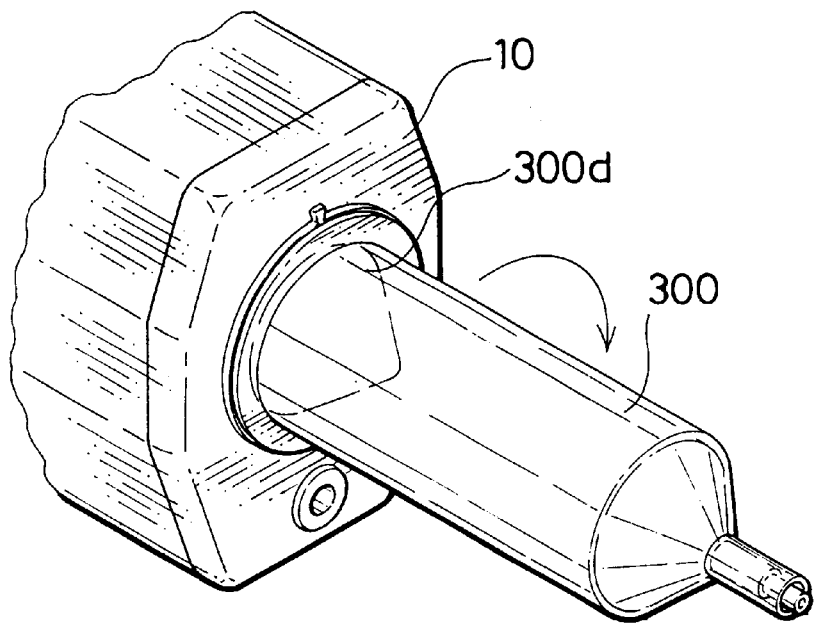
Figure 16:
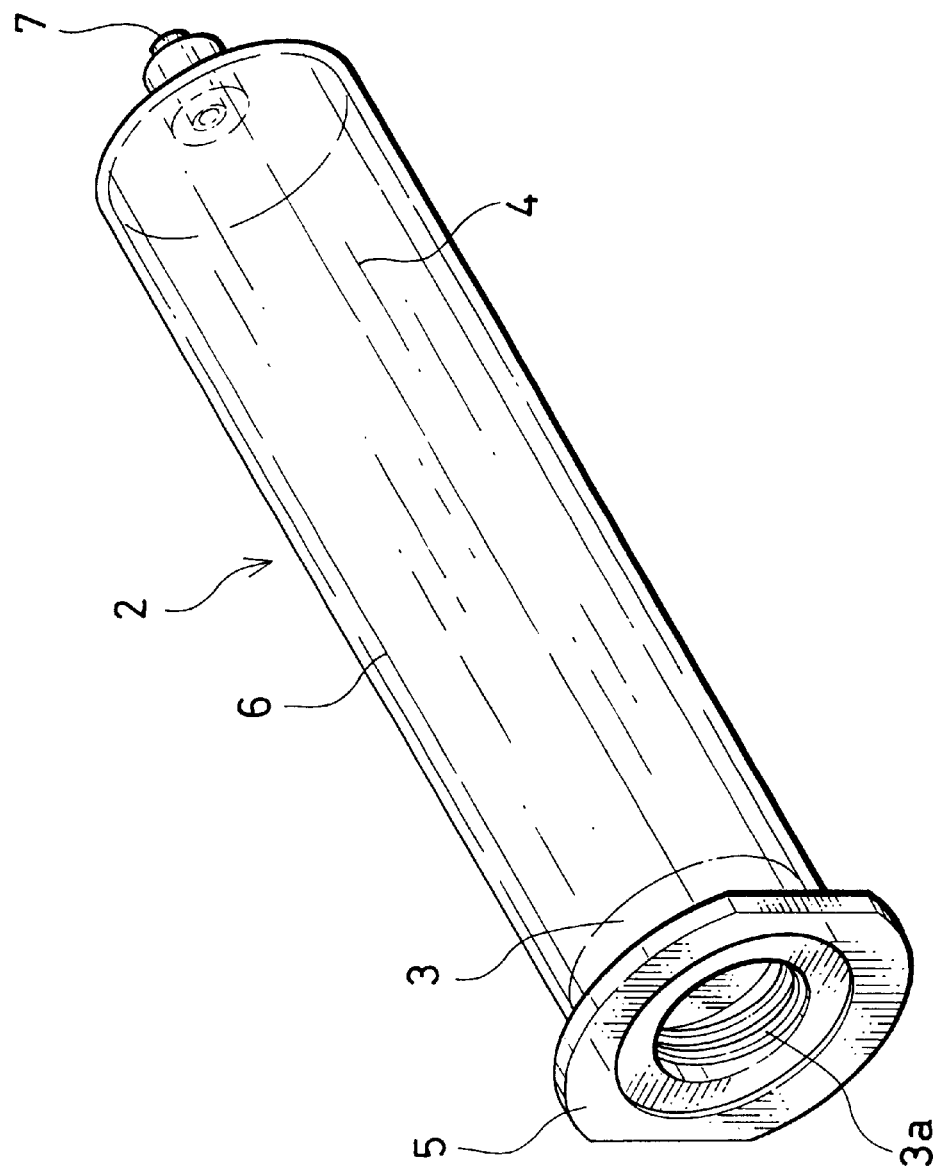
FIG. 16 is a perspective view showing the shape of a syringe according to second prior art.

The rotation member 101 has a cylindrical shape, and is provided on its one end with an oval window part 101b which can receive a head portion 11a (see FIG. 14) of the same shape as the window part 101b provided on a connection part of the plunger 11. "Head portion 11a is coupled to plunger 11 by a neck portion 11b which has a diameter smaller than the minimum width of head portion 11a (see FIG. 3)" The rotation member 101 is further provided on its other end with an opening window 101e which can receive the core member 102.

Further, a pair of elongated grooves 101c are formed on opposite positions of the outer peripheral surface of the rotation member 101, and circular grooves 101d are provided on both end portions of the elongated grooves 101c respectively.

The core member 102 has a cylindrical body part 102a which is provided on its one end with an oval groove part 102b of the same shape as the head portion 11a of the aforementioned plunger 11. The body part 102a is further provided with a pinhole 102i for receiving a pin 102e along the longitudinal direction of the groove part 102b, a ball hole 102d for receiving a ball 102f, a spring 102g and a set screw 102h along a direction perpendicular to the pinhole 102i, and screw holes 102c for fixing the male screw member 103 through machine screws 103c.

When the core member 102 is received in the rotation member 101, both ends of the pin 102e project into the elongated grooves 101c and guide the elongated grooves 101c, so that the rotation member 101 is rotatable by 90° clockwise or anticlockwise along the outer peripheral surface of the core member 102. The ball 102f, which is engageable in the circular grooves 101d from the interior, is engaged in either circular groove 101d upon rotation of the rotation member 101 by 90°, thereby preventing the rotation member 101 from unpreferable rotation caused by vibration or the like while attaining click feeling.

The male screw member 103 has a disc part 103a and a male screw part 103b which is fitted with a female screw part 3a provided on the piston 3 of the syringe 2. The male screw member 103 is fixed to the core member 102 with machine screws 103c passing through screw holes 103d, with interposition of spacers 104. The male screw member 103 is preferably integrated with the core member 102.

Figure 3:
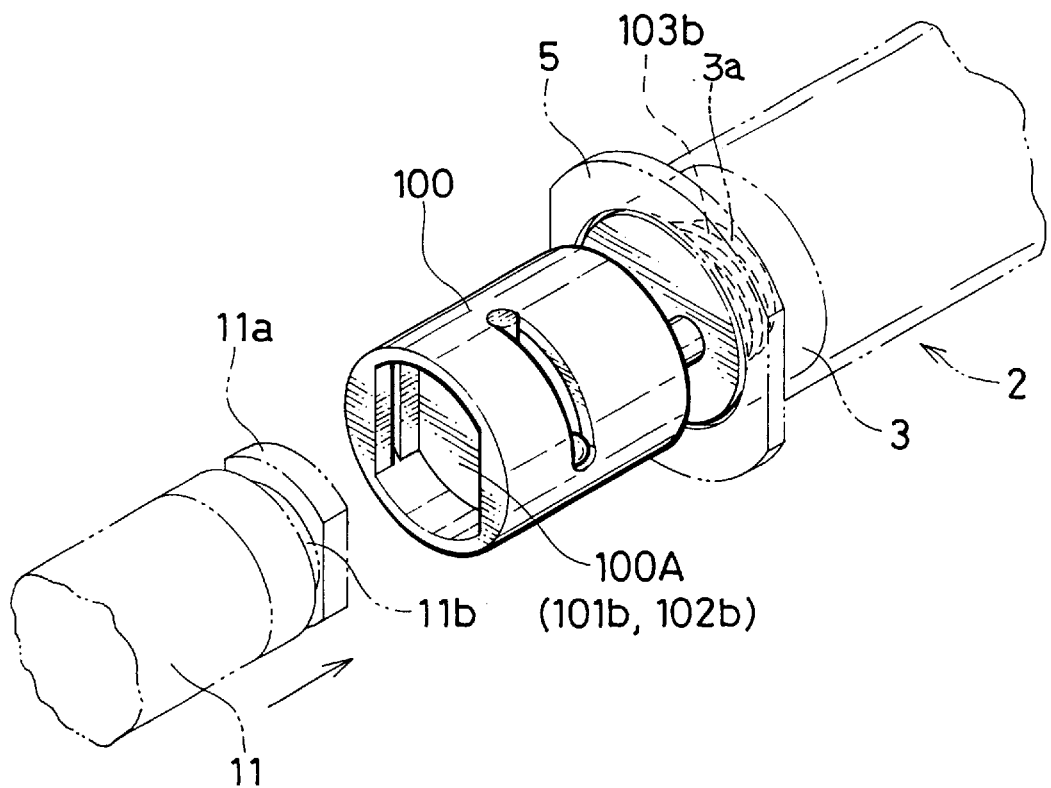
FIGS. 3 and 4 are first and second diagrams showing an operation of the piston adaptor according to the present invention.
Figure 4:
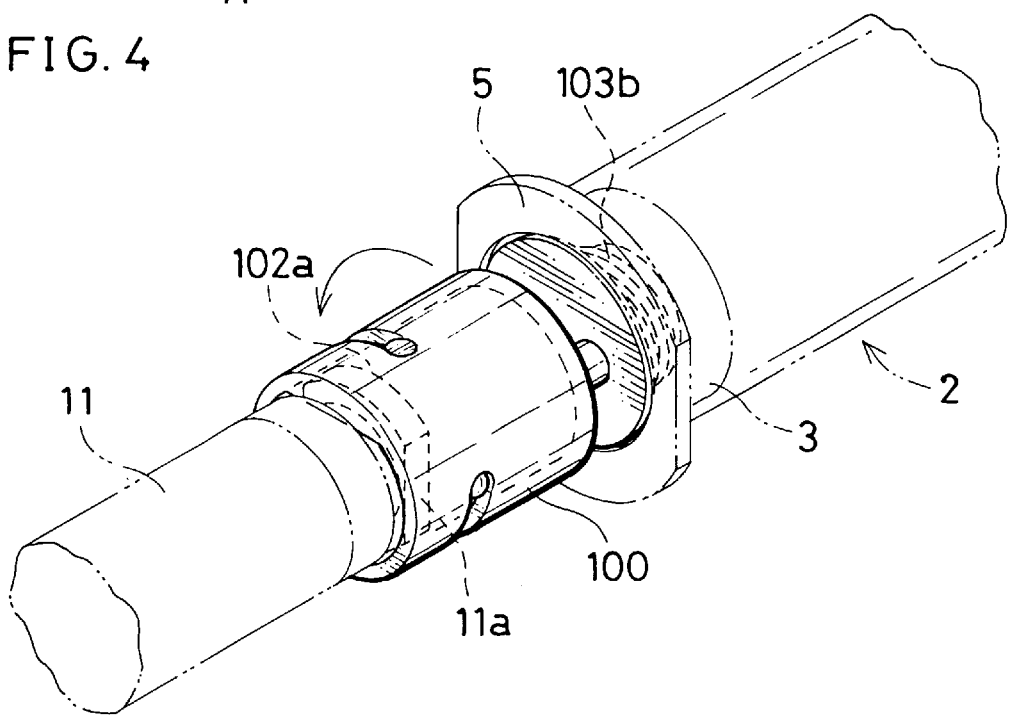

With reference to FIGS. 3 and 4, a state of connecting the plunger 11 with the piston 3 by the piston adaptor 100 is now described.

First, the male screw part 103b of the piston adaptor 100 is fitted with the female screw part 3a provided on the piston 3, as shown in FIG. 3.

On the other hand, the window part 101b of the rotation member 101 is aligned with the groove part 102b of the core member 102, thereby defining a connection window 100A.

Referring to FIG. 4, the head portion 11a of the plunger 11 is inserted in the connection window 100A, and the rotation member 101 of the piston adaptor 100 is rotated by about 90° along arrow. Thus, the head portion 11a of the plunger 11 is connected to the piston adaptor 100.

Figure 5:
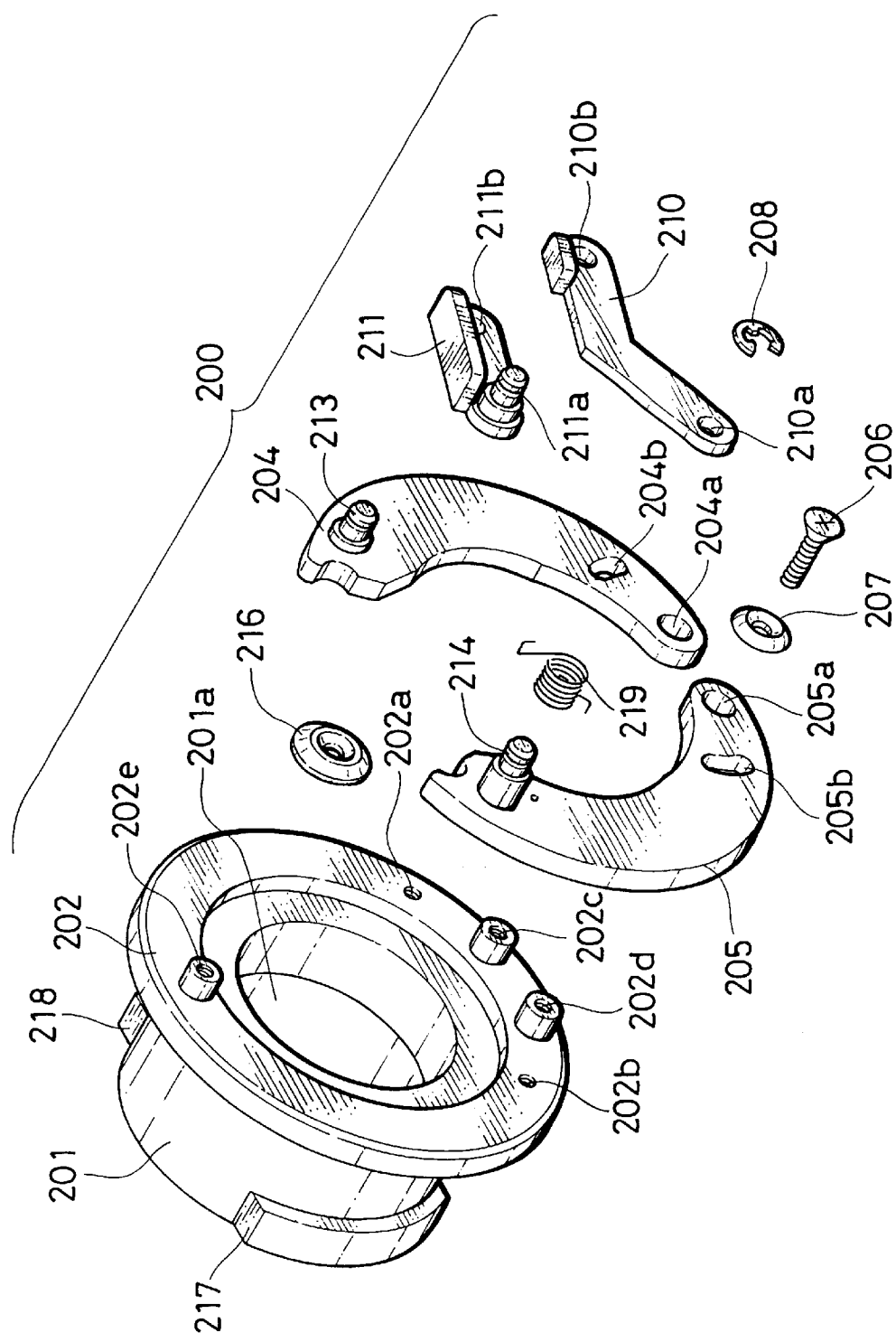
FIG. 5 is a perspective view showing the structure of a syringe adaptor according to the present invention.

With reference to FIG. 5, the structure of the syringe adaptor 200 is now described.

The syringe adaptor 200 has a body part 201 having an opening 201a. The body part 201 is provided on its one end with a pair of projections 217 and 218 which are engaged with convex parts 13 (see FIG. 14) provided on an inner peripheral surface 14 of an opening 12 of the injection head 11 for fixing the syringe adaptor 200 itself to the injection head 11, on positions opposed to each other along the peripheral surface of the body part 201.

The body part 201 is further provided on its other end with a base part 202, a flange receiving part 203 supporting the flange part 5 (see FIG. 1) of the syringe 2 from the rear end and the outer side surface, and a pair of holding members 204 and 205 covering the flange part 5 from the front end of the syringe 2 thereby supporting the flange part 5 along with the flange receiving part 203 while holding the body part of the syringe 2 along its outer peripheral surface.

The holding members 204 and 205 are rotatably fixed to the body part 201 through fixing holes 204a and 205a, which are provided in first ends thereof, with screws 206 and washers 207 through screw holes 202c and 202d provided on the base part 202 respectively.

The holding members 204 and 205 are provided with slots 204b and 205b for limiting open states thereof in the vicinity of the fixing holes 204a and 205a respectively, while the screws 206 and the washers 207 are mounted through screw holes 202a and 202b which are provided on the base part 202.

Further, a first lever 210 for generating force for holding the body part of the syringe 2 by the holding members 204 and 205 is rotatably mounted on a second end of the holding member 204 with a pin 213 and a scotch 208 through a pinhole 210a which is provided on the first lever 210. Similarly, a second lever 211 is rotatably mounted on a second end of the holding member 205 with a pin 214 and a scotch 208 through a pinhole 211b which is provided on the second lever 211.

The first and second levers 210 and 211 are rotatably connected with each other through a pinhole 210b provided on the first lever 210, a pin 211a and the scotch 208. The pin 214 of the first lever 210 is fitted with a spring 219, for regularly maintaining the holding members 204 and 205 in maximum open states when the same are not locked.

In addition, a guide 216 is mounted on a screw hole 202e which is provided in the base part 202 with the screws 206 in the contact portions of the holding members 204 and 205, thereby limiting axial movements of the holding members 204 and 205.

An operation of fixing the syringe 2 through the syringe adaptor 200 having the aforementioned structure is now described with reference to FIGS. 6 and 7.

Figure 6:
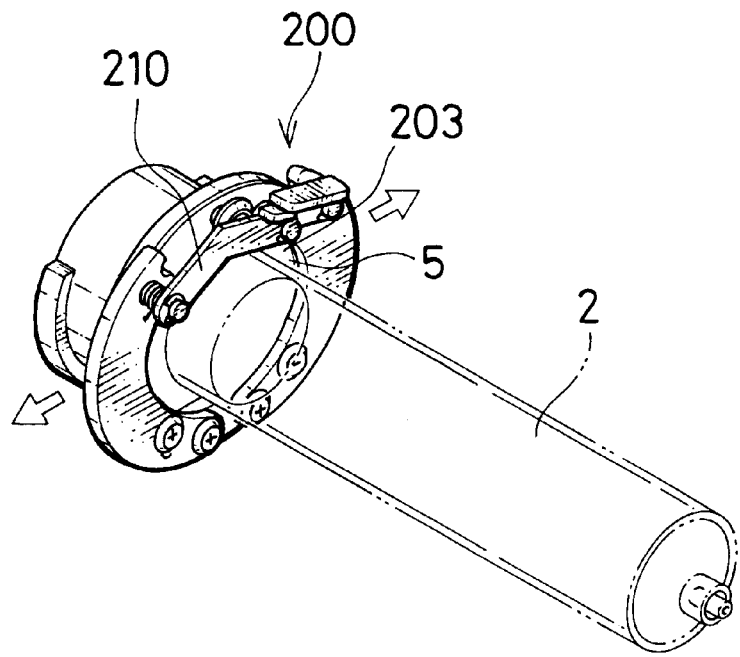
FIGS. 6 and 7 are first and second diagrams showing an operation of mounting the syringe adaptor according to the present invention.

Referring to FIG. 6, the flange part 5 of the syringe 2 is positioned on the flange receiving part 203 which is provided on the syringe adaptor 200.

Figure 7:
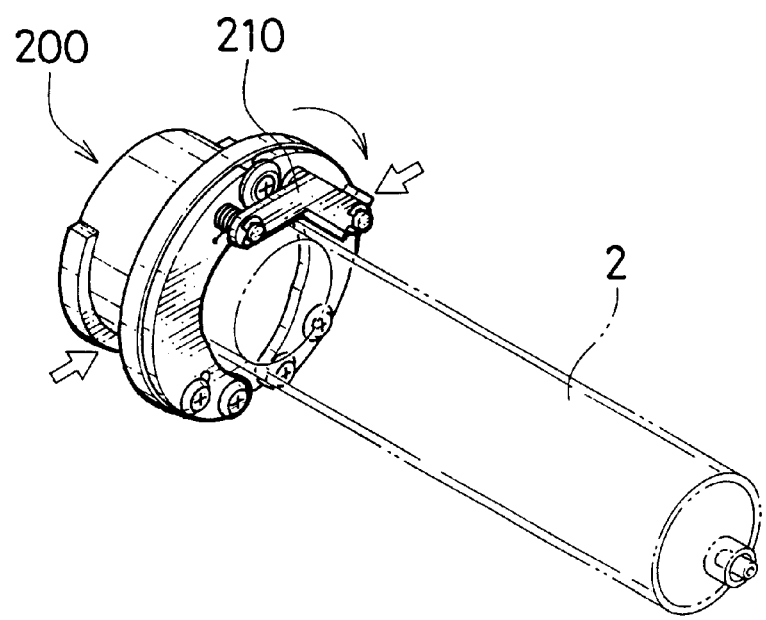

Referring to FIG. 7, the first lever 210 of the holding member 204 is rotated clockwise, thereby holding the body part of the syringe 2 with the holding members 204 and 205. At this time, the rear end and the outer side of the flange part 5 of the syringe 2 are entirely covered with the flange receiving part 203 and the holding members 204 and 205, while the front side thereof is substantially covered.

The procedure of attaching the syringe 2 to the injection head 10 with the auxiliary appliance 1 for syringe fixation having the piston adaptor 100 and the syringe adaptor 200 is now described with reference to FIGS. 8 to 10.

Figure 8:
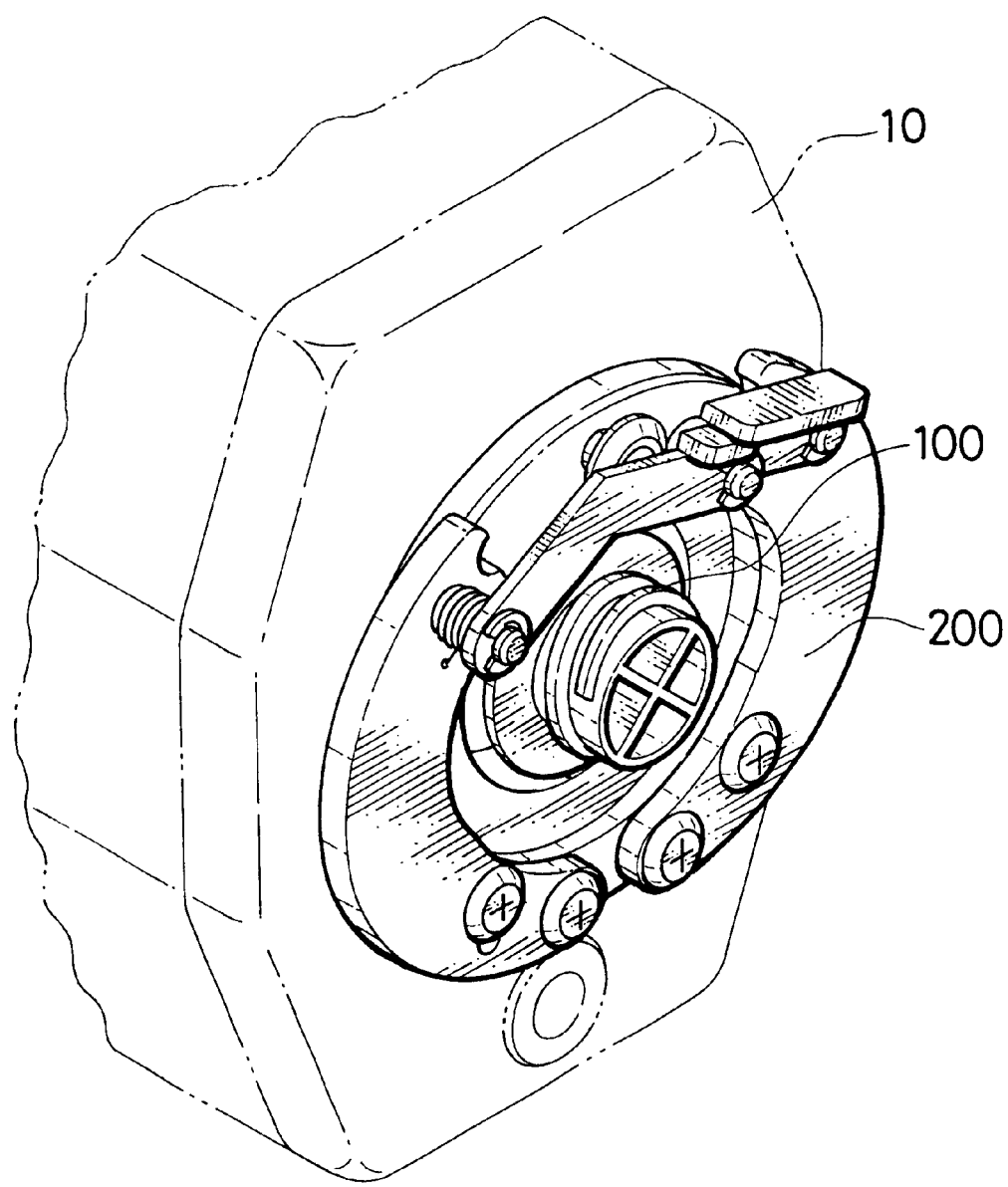
FIGS. 8 to 10 are first to third diagrams showing a procedure of mounting the auxiliary appliance for syringe fixation according to the present invention.

Referring to FIG. 8, the syringe adaptor 200 is mounted on the injection head 10, while the piston adaptor 100 is mounted on the plunger 11.

Figure 9:
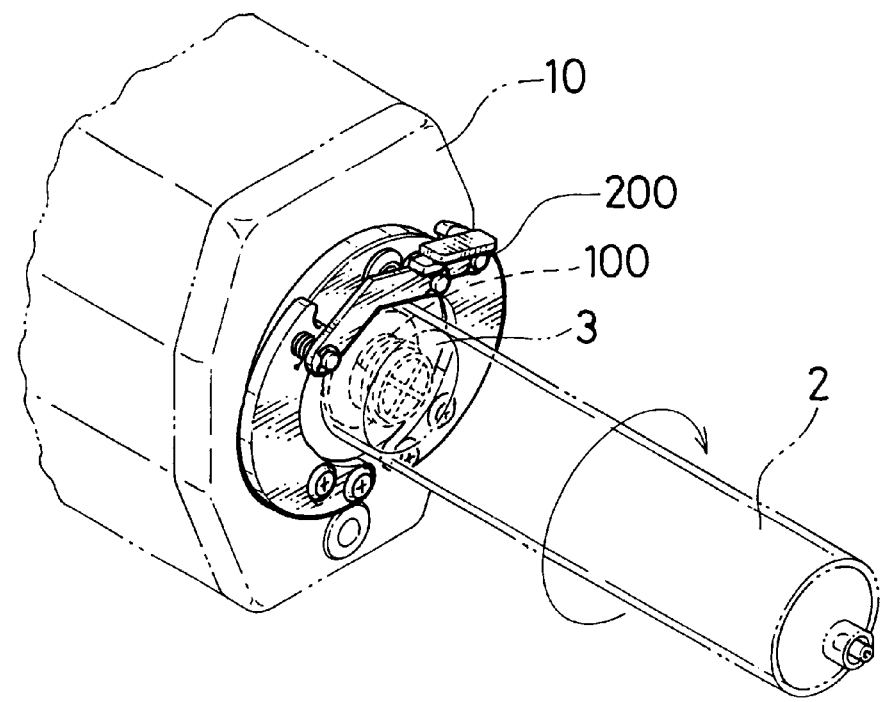

Referring to FIG. 9, the syringe 2 is rotated and the male screw part 103b of the piston adaptor 100 is fitted with/connected to the female screw part 3a of the piston 3 in open states of the holding members 204 and 205 of the syringe adaptor 200.

Figure 10:
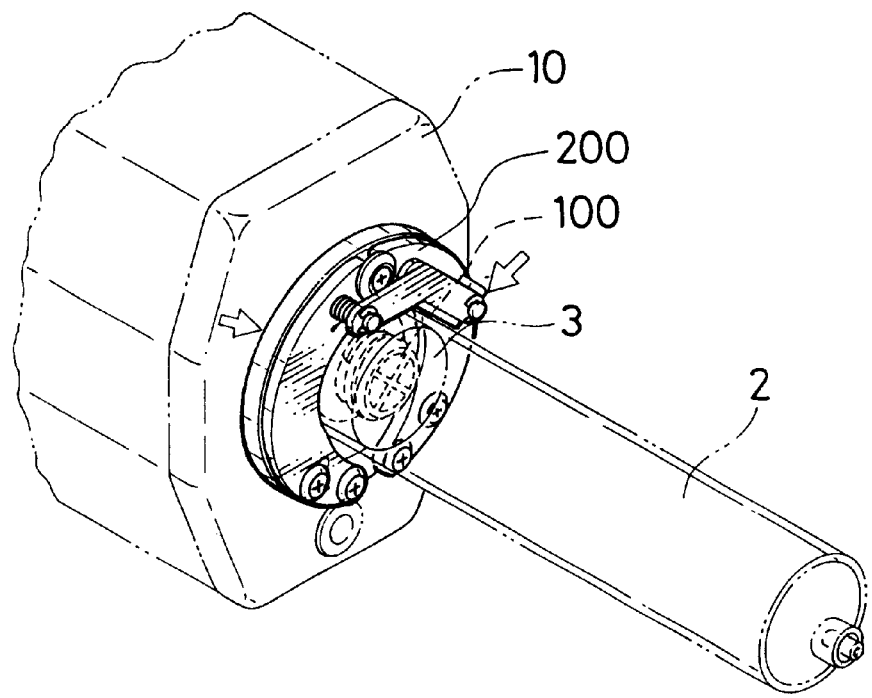
Figure 11:
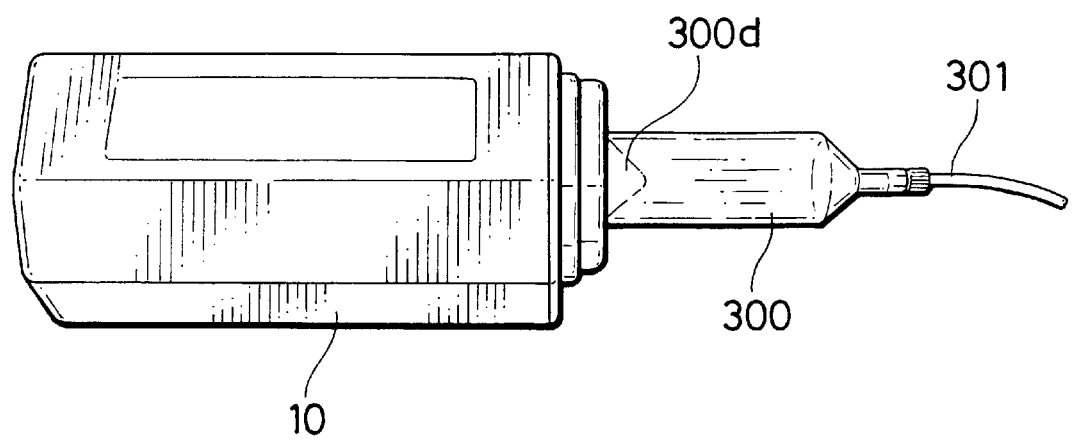
FIGS. 11 to 12 are first and second diagrams showing an operation of an injection head.
Figure 12:
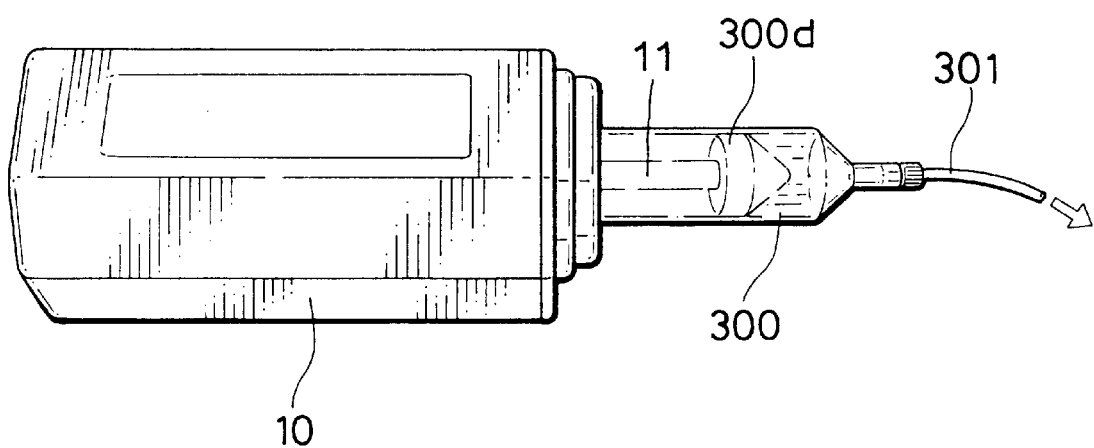
Figure 13:
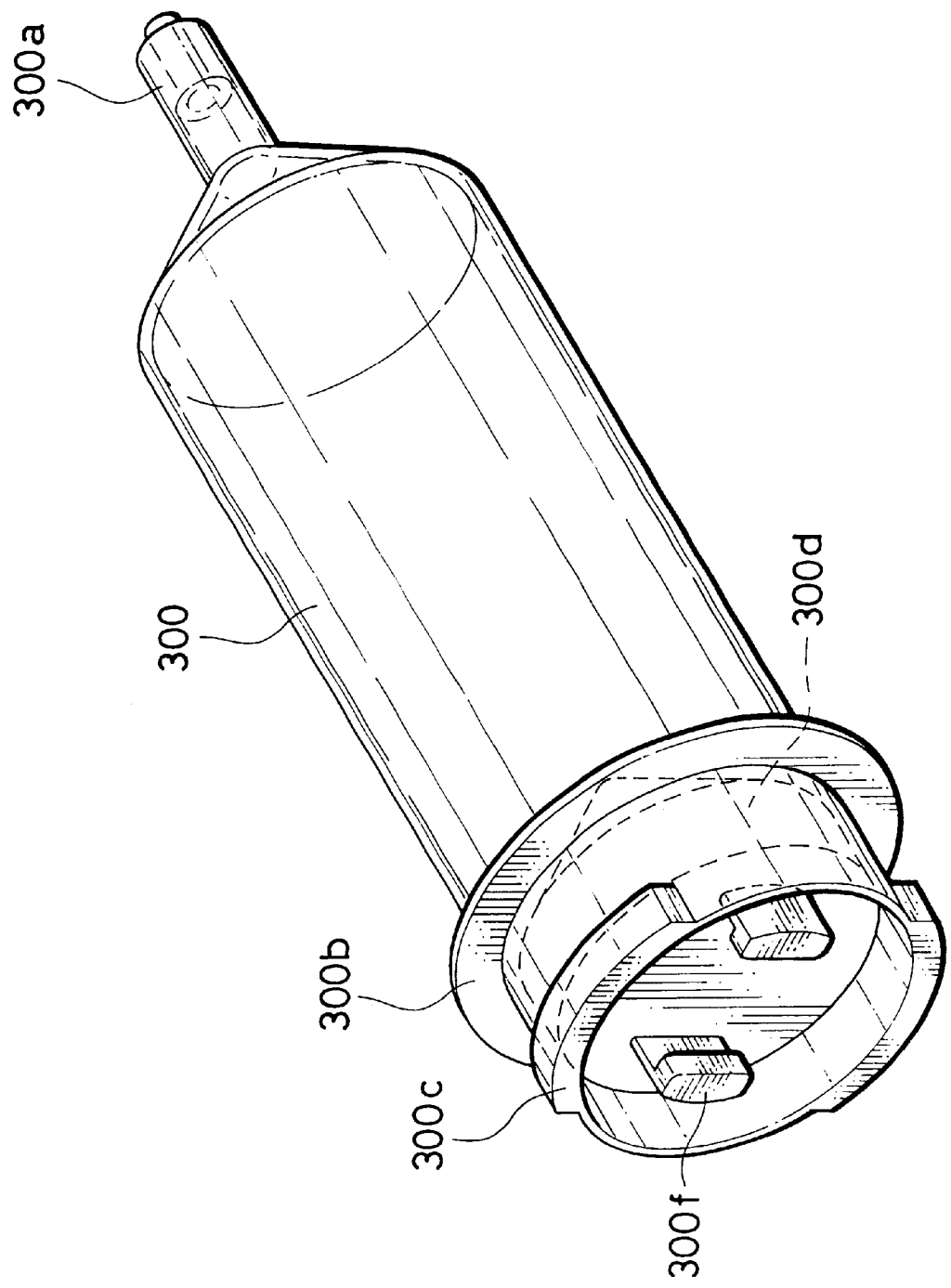
FIG. 13 is a perspective view showing the shape of a syringe according to first prior art.

Thereafter the body part of the syringe 2 is fixed through the holding members 204 and 205 with the first and second levers 210 and 211, as shown in FIG. 10. Thus, the syringe 2 is completely attached to the injection head 10.

Thus, according to this embodiment, it is possible to connect a syringe, having a shape which cannot be directly connected to the injection head 10, to the injection head 10 by the auxiliary appliance 1 for syringe fixation having the syringe adaptor 200 and the piston adaptor 100.

Consequently, two types of syringes can be connected to a single injection head 10, whereby convenience for doctors and patients can be improved in the medical field.

The embodiment described above must be regarded as being not restrictive but illustrative in all points. While the appliance according to this embodiment connects the syringe with the piston through fitting of screws, the present invention is not restricted to this but another well-known connection structure may alternatively be employed. The scope of the present invention is shown not by the above description but by the scope of claims, and is intended to include equivalent meaning as the scope of claims and all modifications within the scope.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An auxiliary appliance for syringe fixation, for fixing a syringe having a cylindrical body part, and comprising an injection port and a flange respectively defining an opening on each of front and rear ends thereof, and adapted for sealing a liquid in an internal space defined by a piston having a connection part on the flange side in the interior of the syringe cylindrical body part, to an injection head provided with an opening having an inner peripheral surface provided with an engaging convex part and comprising a plunger having a connection part including a body part with a neck portion smaller than the diameter of its body part and a substantially oval head portion connected to the neck portion with a curved portion having a radius of curvature identical to that of the plunger body part on its forward end for moving the piston in the syringe toward the forward end of the syringe in the opening and injecting the liquid from the syringe through the injection port, said auxiliary appliance for syringe fixation comprising:
a syringe adaptor for fixing the flange of the syringe to the injection head, said syringe adaptor having a flange receiving part adapted to support a rear surface and an outer surface of the flange and a pair of pivotable holding members pivotable about a pivot axis parallel to the cylindrical body part of the syringe, said pivotable holding members having a disengaged position, and an engaged position for engaging a front surface of the flange and an outer peripheral surface of the syringe cylindrical body to hold the syringe within the flange receiving part; and a piston adaptor receivable within said syringe adaptor for connecting the piston to the plunger.

2. The auxiliary appliance for syringe fixation in accordance with claim 1, wherein
said syringe adaptor further includes:
a cylindrical body part having a first end and a second end, said flange receiving part and said pair of holding members being positioned at said first end, and
a projection extending from said second end of said syringe adaptor cylindrical body part for engaging with the engaging convex part and for fixing said syringe adaptor to the injection head.

3. The auxiliary appliance for syringe fixation in accordance with claim 1, wherein
said piston adaptor has a first side and a second side, and wherein said piston adaptor comprises:
a connection part at said first side for engaging the connection part of the piston, and
a connection receiving part at said second side for receiving/fixing the connection part of the forward end of the plunger.

4. An auxiliary appliance for syringe fixation, for fixing a syringe having a cylindrical body part, and comprising an injection port and a flange respectively defining an opening on each of front and rear ends thereof, and adapted for sealing a liquid in an internal space defined by a piston having a connection part on the flange side in the interior of the syringe cylindrical body part, to an injection head provided with an opening having an inner peripheral surface provided with an engaging convex part and comprising a plunger having a connection part including a body part with a neck portion smaller than the diameter of its body part and a substantially oval head portion connected to the neck portion with a curved portion having a radius of curvature identical to that of the plunger body part on its forward end for moving the piston in the syringe toward the forward end of the syringe in the opening and injecting the liquid from the syringe through the injection port, said auxiliary appliance for syringe fixation comprising:

a syringe adaptor for fixing the flange of the syringe to the injection head, said syringe adaptor having a flange receiving part adapted to support a rear surface and an outer surface of the flange and a pair of pivotable holding members having a disengaged position, and an engaged position for engaging a front surface of the flange and an outer peripheral surface of the syringe cylindrical body to hold the syringe within the flange receiving part; and a piston adaptor receivable within said syringe adaptor for connecting the piston to the plunger, said piston adaptor including:
a first side and a second side,
a connection part at said first side for engaging the connection part of the piston, and
a connection receiving part at said second side for receiving/fixing the connection part of the forward end of the plunger;

wherein said connection receiving part comprises:
a substantially cylindrical core member having the same radius of curvature as the curved portion of the head portion of the plunger, and
a cylindrical rotation member rotatable along the outer peripheral surface of said core member,
said rotation member has a substantially oval shaped window part of the same shape as the head portion on one side, said window part being capable of receiving the head portion of the connection part of the plunger, and
said core member has a groove part for receiving the head portion on one side, for fixing the head portion of the plunger to said groove by receiving the head portion after aligning said window part and said groove part with each other and rotating said rotation member by about 90°.

5. An arrangement for attachment to a syringe injection head provided with an opening having an inner peripheral surface provided with an engaging convex part and comprising a plunger having a connection part including a body part with a neck portion smaller than the diameter of its body part and a substantially oval head portion connected to the neck portion with a curved portion having a radius of curvature identical to that of the plunger body part on its forward end for moving the piston, said arrangement comprising:

a syringe having a cylindrical body part, and comprising an injection port and a flange respectfully defining an opening on each of a front and rear end thereof, said syringe being adapted for scaling a liquid in an internal space defined by a piston having a connection part on the flange side in the interior of the syringe cylindrical body part; and an auxiliary appliance for syringe fixation including:
a syringe adaptor for fixing the flange of the syringe to the injection head, said syringe adaptor having a flange receiving part adapted to support a rear surface and an outer surface of the flange and a pair of pivotable holding members having a disengaged position, and an engaged position for engaging a front surface of the flange and an outer peripheral surface of the syringe cylindrical body to hold the syringe within the flange receiving part, and
a piston adaptor receivable within said syringe adaptor for connecting the piston to the plunger;

wherein the piston is movable by the plunger within the syringe toward the forward end thereof to inject the liquid from the syringe through the injection poll.

* * * * *